(12) United States Patent
Walker et al.

(10) Patent No.: US 8,509,381 B2
(45) Date of Patent: Aug. 13, 2013

(54) PATIENT POSITIONING SYSTEM FOR PANORAMIC DENTAL RADIATION IMAGING SYSTEM

(75) Inventors: Donald Walker, Mundelein, IL (US); Arkady Kantor, Buffalo Grove, IL (US); Lyubomir L Cekov, Rolling Meadows, IL (US); Alan P. Krema, Naperville, IL (US)

(73) Assignee: Midmark Corporation, Versailles, OH (US)

( * ) Notice: Subject to any disclaimer, the term of this patent is extended or adjusted under 35 U.S.C. 154(b) by 538 days.

(21) Appl. No.: 12/638,600

(22) Filed: Dec. 15, 2009

(65) Prior Publication Data

US 2011/0142197 A1   Jun. 16, 2011

(51) Int. Cl.
*A61B 6/14* (2006.01)
*A61B 6/08* (2006.01)

(52) U.S. Cl.
USPC .............................. 378/39; 378/196; 378/206

(58) Field of Classification Search
USPC ............................................ 378/39, 196, 206
See application file for complete search history.

(56) References Cited

U.S. PATENT DOCUMENTS

| | | | |
|---|---|---|---|
| 4,741,007 A | 4/1988 | Virta et al. | |
| 4,782,503 A * | 11/1988 | Molitor et al. | 378/169 |
| 4,907,251 A * | 3/1990 | Mork et al. | 378/39 |
| 5,224,140 A * | 6/1993 | Virta et al. | 378/38 |
| 5,425,065 A | 6/1995 | Jarvenin | |
| 5,511,106 A | 4/1996 | Doebert et al. | |
| 5,692,027 A * | 11/1997 | Yoshimura et al. | 378/38 |
| 5,732,119 A | 3/1998 | Kopsala | |
| 5,921,927 A * | 7/1999 | McArdle | 600/425 |
| 6,289,074 B1 * | 9/2001 | Arai et al. | 378/4 |
| 6,466,641 B1 | 10/2002 | Virta et al. | |
| 6,510,196 B2 | 1/2003 | Laner | |
| 6,553,095 B2 | 4/2003 | Rinaldi et al. | |
| 6,731,717 B2 | 5/2004 | Kopsala | |
| 6,744,847 B2 | 6/2004 | Martti | |
| 6,829,326 B2 | 12/2004 | Woods et al. | |
| 6,891,921 B2 | 5/2005 | Kopsala | |
| 7,421,059 B2 * | 9/2008 | Suzuki et al. | 378/39 |
| 7,534,038 B2 * | 5/2009 | Rotondo et al. | 378/205 |
| 7,787,586 B2 * | 8/2010 | Yoshimura et al. | 378/4 |
| 2006/0227939 A1 * | 10/2006 | Walker et al. | 378/208 |
| 2006/0240378 A1 * | 10/2006 | Weinstein et al. | 433/76 |
| 2009/0274267 A1 * | 11/2009 | Mandelkern et al. | 378/39 |
| 2009/0285356 A1 * | 11/2009 | Thoma et al. | 378/20 |
| 2011/0142197 A1 * | 6/2011 | Walker et al. | 378/38 |

* cited by examiner

*Primary Examiner* — Thomas R Artman
(74) *Attorney, Agent, or Firm* — Wood, Herron & Evans, LLP

(57) ABSTRACT

A patient positioning system for a panoramic dental radiation imaging system, including an upright support, and a patient positioning arm with chin rest mounted thereto. Wands are each rotatably connected to the patient positioning arm and connected together so as to move at identical angles of rotation, but in the opposite direction. Lasers, including a mid-sagittal, a Frankfort Plane, two cuspid, and one toe laser, each providing a line of visible laser light directed at a respective area of a patient's face, or at the floor, assist a technician in properly positioning the patient. A mirror is mounted to the upright support by a mechanism that permits the mirror to be pivoted outward from the support, in either of two directions, so as to enable the technician to see the lasers on the patient's face from the technician's position on either side of the positioning arm.

15 Claims, 15 Drawing Sheets

PATIENT POSITIONING SYSTEM FOR PANORAMIC DENTAL RADIATION IMAGING SYSTEM

BACKGROUND OF THE INVENTION

This invention relates to dental radiation imaging systems, and in particular to systems for positioning a patient with respect to a radiation source and detector so as to produce panoramic images.

Panoramic dental radiation imaging is used to obtain images of a patient's teeth in an orthogonal manner. Since the dental arch is not a circular shape, the rotation of the arm to which the radiation source and detector are attached must be adjusted in the course of the imaging in order to achieve the proper orthogonal imaging. Conventional panoramic radiation apparatuses are characterized in that the radiation source is arranged to orbit about the patient's skull, whereby the dental arch can be imaged by means of a radiation detector orbiting on the opposite side of the skull. The function of the rotating mechanism of a panoramic radiation apparatus is to direct the radiation beam through the patient's jaw at a desired angle and to keep the radiation detector at a particular distance and orientation with respect to the object being imaged.

The radiation source of the panoramic radiation system and the rotating mechanism of its radiation detector must be capable of forming an image of the dental arch. During the rotational movement, the center of rotation is moved in order to ensure orthgonality of the radiation beam on the dental arch, constant magnification, and continuity of motion. The rotating mechanism must be able to accomplish the desired orbital movement of the center of rotation in a horizontal plane and provide vertical support to the entire apparatus so that the desired orbit can be implemented with accuracy. Such orbital movement can be achieved by virtue of different conventional rotating mechanisms, such as those disclosed in U.S. Pat. Nos. 4,741,007 and 6,466,641.

Also important is the proper positioning of a patient with respect to the radiation imaging apparatus, such that the rotation of the radiation source and detector about the patient's skull is in proper alignment with the dental arch. Also, in order to ensure a clear image, the patient must remain still during the imaging. Conventional mechanisms for patient positioning include platforms on which a patient may place his chin, such as that shown in U.S. Pat. No. 6,466,641. However, while these types of platforms aid in proper vertical alignment (along the Z axis) of the skull to adjust the height of the radiation source and detector, it does not provide for proper forward-backward positioning (the Y axis), positioning in right-left direction (the X axis), stabilizing the patient in the apparatus, or providing a convenient way for a technician to assess proper positioning. Other conventional systems may include arms to guide the top of the head, such as those shown in U.S. Pat. Nos. 5,511,106 and 6,510,196. Again, while these mechanisms may provide for position in one or more of the X, Y, and Z axes, neither provides positioning in all three directions, along with stabilization of the patient and easy assessment of position by the patient and or the technician.

The present invention relates to improvements to the apparatus described above and to solutions to some of the problems raised or not solved thereby.

SUMMARY OF THE INVENTION

The present invention relates to panoramic dental radiation imaging, and in particular to a patient positioning system for a panoramic dental radiation imaging system to achieve desired positioning of the patient for rotation of a radiation source and receiver about a patient's skull, in which positioning of the patient along all necessary axes, stabilization of the patient in the proper position, and easy and convenient mechanisms to assess proper positioning are provided.

The invention provides a patient positioning system for a panoramic dental radiation imaging system, the imaging system having a radiation source and a radiation sensor. The positioning system includes an upright support supporting the radiation source and radiation sensor. A patient positioning arm is mounted to the upright support. A chin rest is mounted to the patient positioning arm. A pair of wands are each rotatably connected to the patient positioning arm and connected together so as to move at identical angles of rotation with each other. A pair of cuspid lasers, each providing a laser line directed at a respective side of a patient's face, thereby permitting a technician to position a patient's dentition in the proper position for the functioning of the imaging system. A toe laser projects a line of light on a floor in front of the patient to assist the patient to position his feet, and thereby his body, as desired with respect to the imaging system. A mid-sagittal laser projects a line of light onto the mid-sagittal area of patient's face, and a Frankfort Plane laser projects a line of light onto the Frankfort Plane area of the patient's face, to further assist the technician to position the patient's head as desired with respect to the imaging system.

A mirror is mounted to the upright support by a mechanism that permits the mirror to be rotated outward from the upright support, in two directions, so as to enable the technician to see the lasers on the patient's face from the technician's position on either side of the positioning arm. The mirror mounting mechanism includes a frame, a top base member, and a bottom base member. The frame has a pair of posts spaced apart at the top, and another pair of posts spaced apart at the bottom. Each base member includes a pair of notches which, when the mirror is in a flat position, each fit around a respective one of the posts. The mounting mechanism also includes a pair of plates, and a pair of brackets coupled to the plates, the brackets having slots which allow the brackets to move the distance of the slot length as the brackets slide along the posts, which allows the plates to move to the angled positions. Hinges are coupled to the plates and base members, and capable of rotating about hinge pins. At least one tab is provided on the lower base member, such that when a user pulls on one of the tabs, the hinge tubes coupled to the plates rotate about the hinge pins, and plates on same side of the hinges as tab move the corresponding bracket, allowing movement of the base members and the mirror coupled thereto to an angle in the direction the tab is pulled.

Other objects and advantages of the invention will become apparent hereinafter.

DETAILED DESCRIPTION

Figure 1:
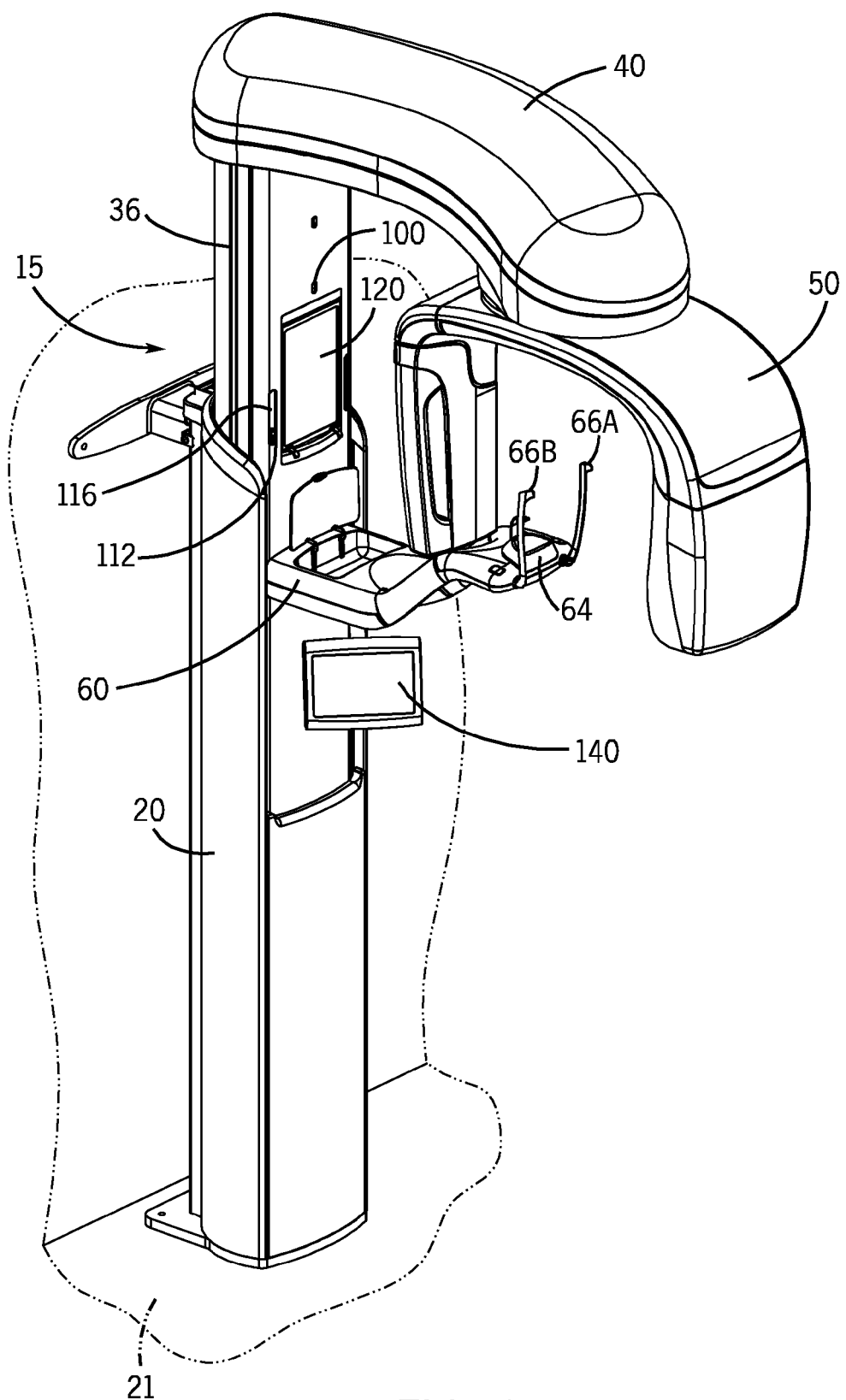
FIG. 1 is a perspective view of a panoramic dental radiation imaging system in accordance with one embodiment of the present invention.

This application is being filed at the same time as a patent application on a motion system for a panoramic dental radiation imaging system, and a patent application on a removable radiation sensor for a dental imaging system, and a design patent application on a dental imaging system, all filed on the same day as this application and assigned to the same assignee. The disclosure of each of those other patent applications is incorporated herein by reference.

One embodiment of a panoramic dental radiation imaging system 10 and patient positioning system therefor is shown in the figures. While the invention may be susceptible to embodiment in different forms, there is shown in the drawings, and herein will be described in detail, certain illustrative embodiments with the understanding that the present disclosure is to be considered an exemplification of the principles of the invention, and is not intended to limit the invention to those as illustrated and described herein. Additionally, features illustrated and described with respect to one embodiment could be used in connection with other embodiments.

FIG. 1 shows a panoramic dental radiation imaging system 10. The radiation imaging system 10 is used for radiation of a dental patient's teeth, and generally includes a radiation source 52 and an optionally removable radiation receiver 54, both supported by an upright support 15. Upright support 15 is preferably formed of an outer column 20, an inner column 30, an overhead arm 40, and a C-arm 50 to which the radiation source 52 and radiation receiver 54 are mounted. The radiation receiver unit 54 may optionally be removably connected to C-arm 50. A patient positioning arm 60 is also mounted to the upright support 15. Outer column 20 may be fixed to a floor 21 and/or a wall 22 by any suitable means such as a support leg 23 to support the radiation imaging system 10.

The patient positioning arm 60 and other elements associated therewith, forming the patient positioning system, ensure that the patient is properly aligned for positioning of the C-arm 50 including the radiation source 52 and receiver 54 for taking of a radiation image of the patient's teeth. Inner column 30 may be movably coupled to outer column 20 to allow movement of the inner column 30 in the vertical, or Z-axis, direction.

Figure 2A:
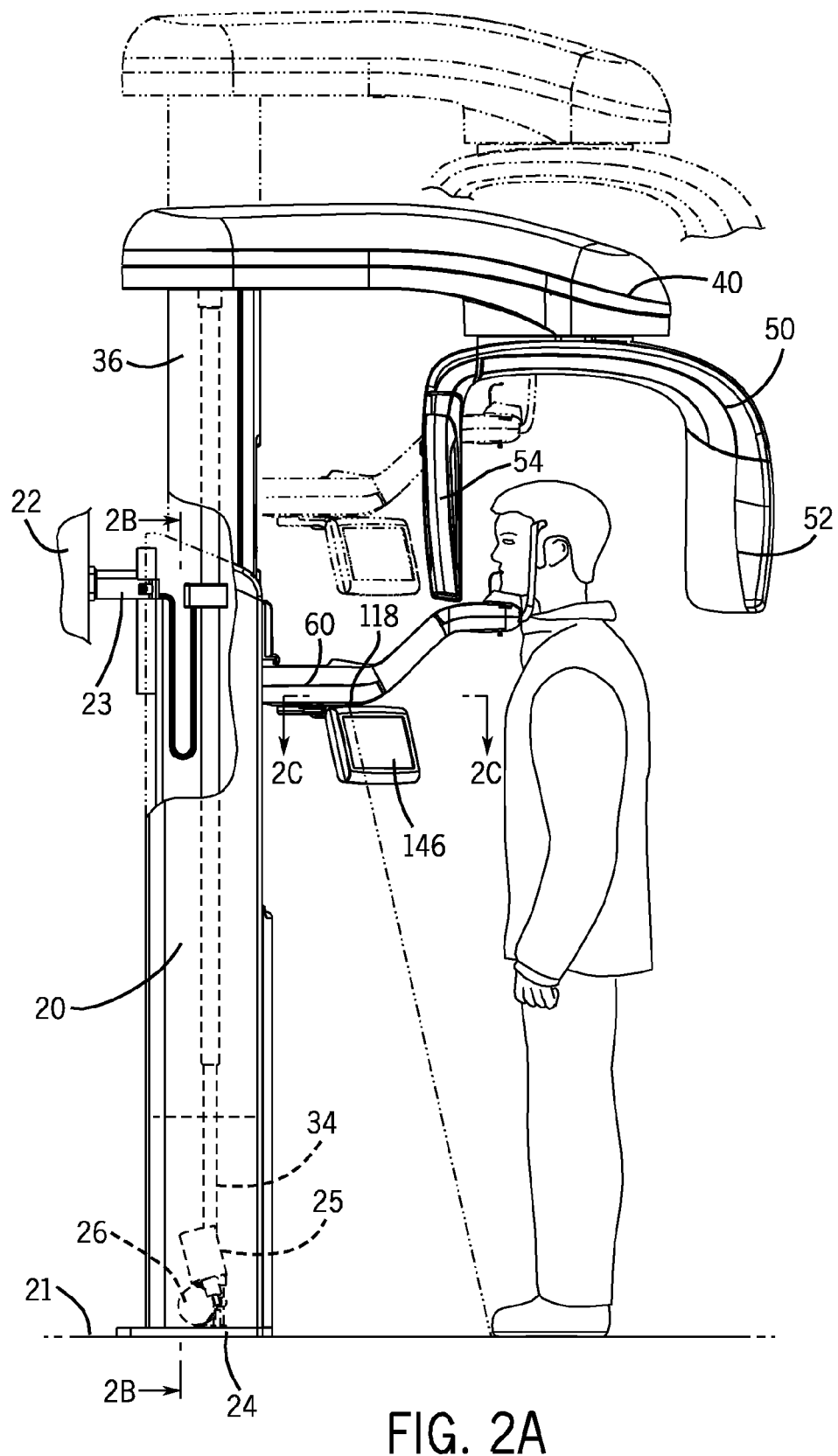
FIG. 2A is a side view of a panoramic dental radiation imaging system in accordance with the embodiment shown in FIG. 1, showing one position of a movable portion of the system in phantom.
Figure 2B:
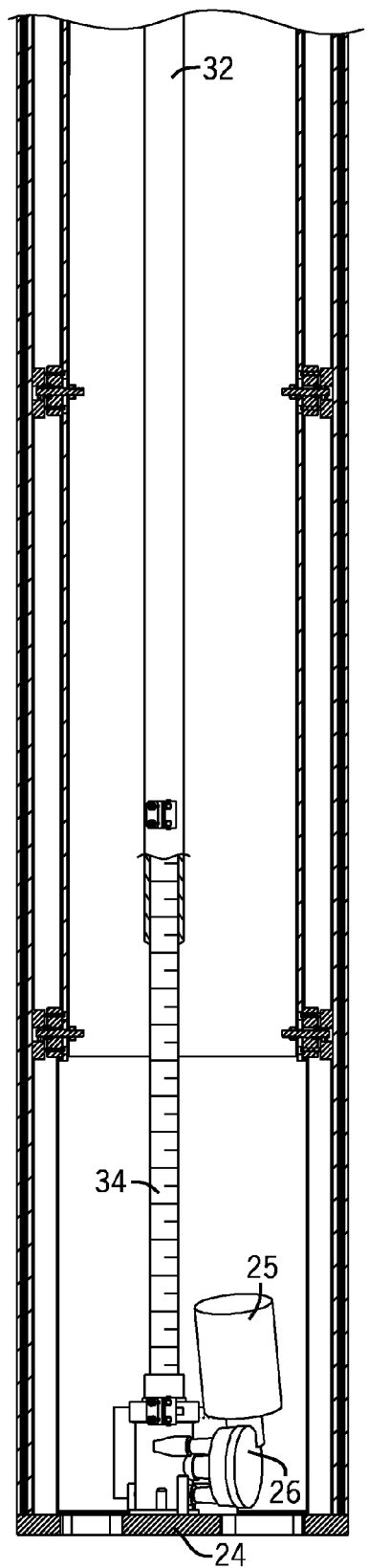
FIG. 2B is cross sectional view taken along line 2B-2B of FIG. 2A.

FIGS. 2A and 2B show the mechanism for vertical movement of the inner column 30. In the embodiment shown, threaded tube 32 is connected to inner column 30, and threaded rod 34 is connected to a base 24 to which outer column 20 is also connected. In this embodiment, tube 32 and rod 34 are threadedly engaged together. A motor 25, shown mounted on the base 24, rotates the rod 34, in this case by means of a gear reducer 26, so as to move the tube 32 up or down depending upon the direction of rotation. Since inner column 30 is connected to tube 32, the up or down movement of the tube moves the inner column up and down along with it, allowing patient positioning arm 60 and C-arm 50 including the radiation source 52 and radiation sensor 54, both coupled to inner column 30, to be adjusted to the height of the particular patient on which the radiation image is to be taken.

Inner column 30 is adjusted in the Z-axis direction for the particular height of the patient, such that patient's chin may relatively comfortably rest on a chin rest 64, positioned on a chin table 61 at or near the distal end of the patient positioning arm 60. Chin rest 64 is positioned on chin table 61 such that the patient's skull is properly aligned along the X-axis for rotation of the C-arm 50 about the skull when the chin is placed in the chin rest 60. Chin rest 64 is mounted to top cover 63 of chin table 61. Chin rest 64 may be shaped to comfortably and securely receive a relatively normal patient's chin, providing stabilization of the patient's head in the proper position. A bite stick 65 may also be coupled to patient positioning arm 60 and flexibly project generally over chin rest 64. The patient can thus engage his front teeth with bite stick 65, while resting his chin on chin rest 64, so as to even more reliably align the dental arch in the correct position for imaging, as well as to maintain a constant head position during imaging.

Figure 2C:
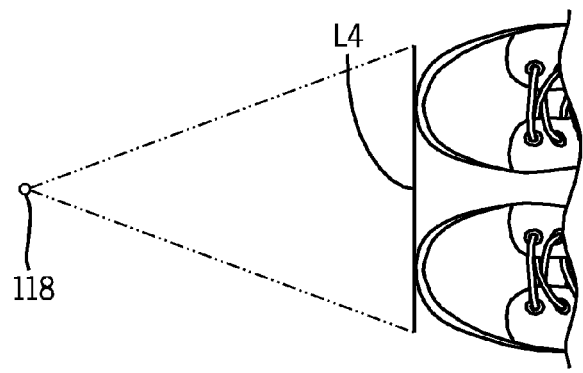
FIG. 2C is a top view of the line of light provided by the toe laser to assist the patient in positioning his feet in a comfortable and stable manner.
Figure 3:
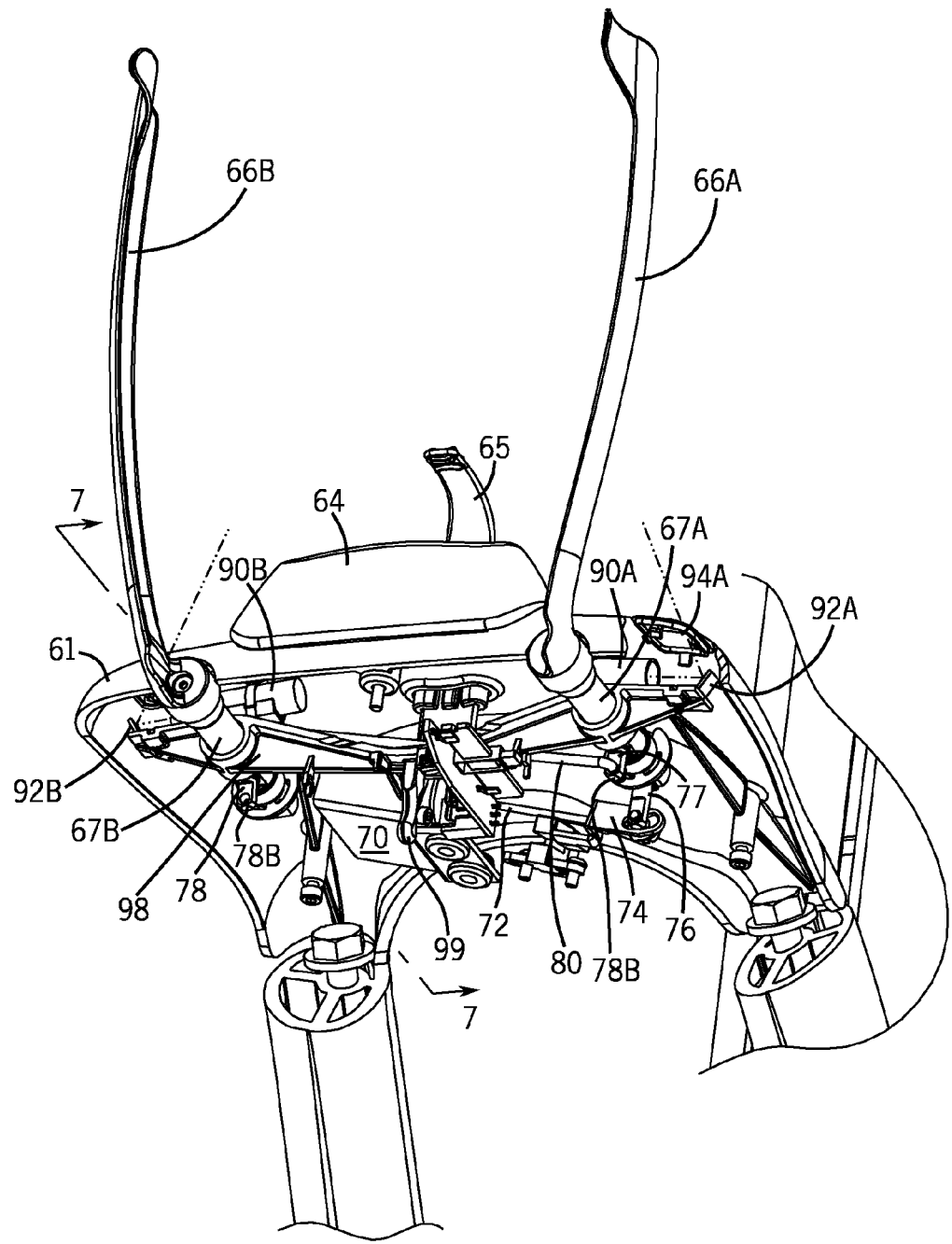
FIG. 3 is a bottom perspective view of a portion the patient positioning arm of a panoramic dental radiation imaging system in accordance with the embodiment of the invention shown in FIG. 1, with a portion of a bottom cover removed to reveal detail, and showing patient positioning wands in a first position.
Figure 4:
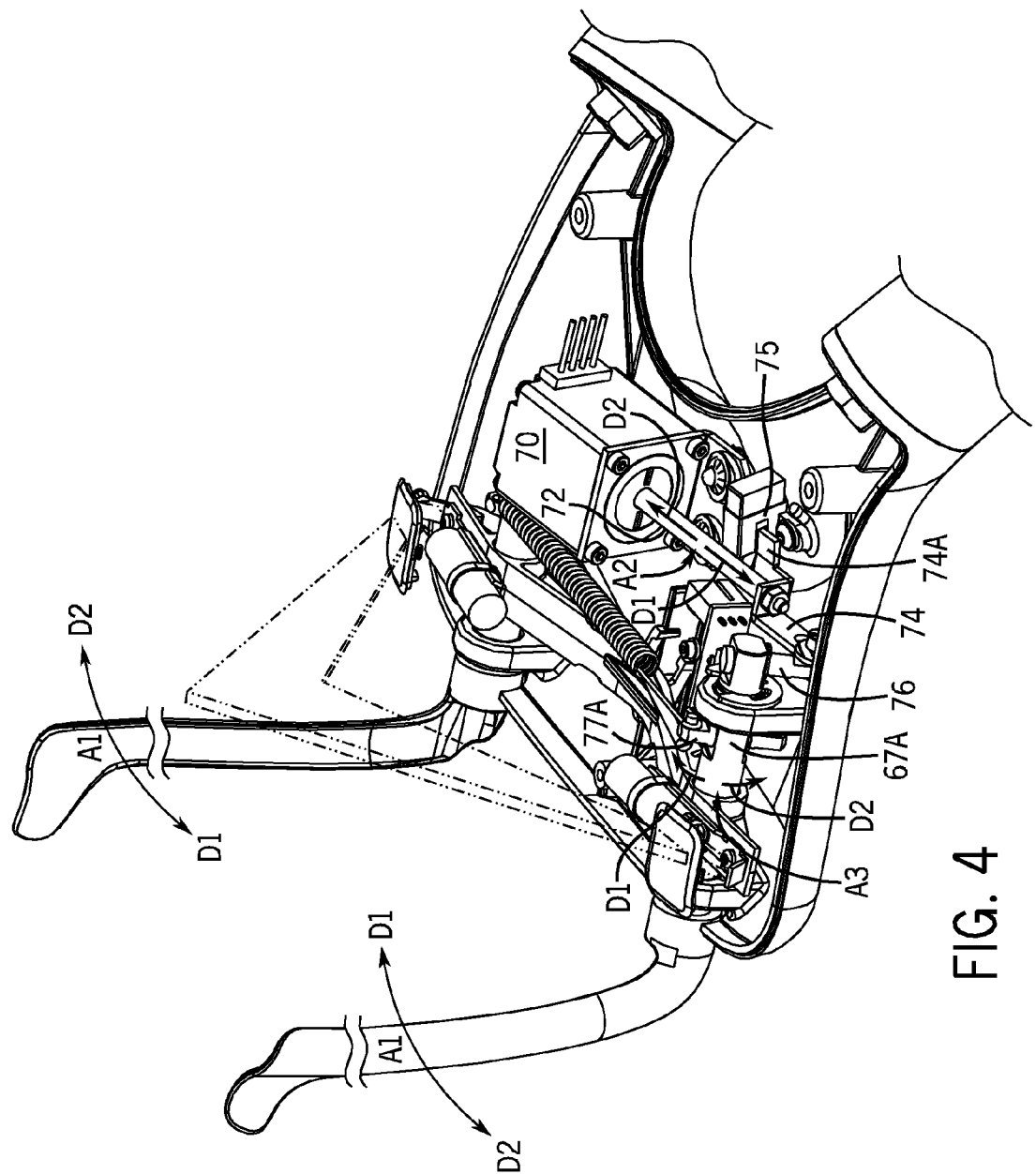
FIG. 4 is a bottom perspective view of a portion the patient positioning arm of a panoramic dental radiation imaging system in accordance with the embodiment of the invention, as shown in FIG. 3, except from a different angle.

To ensure proper positioning of the patient in the right-to-left, or X-axis, direction, to ensure that the patient's head is not tipped to either the right or left side, and to stabilize patient in the proper position, wands 66A, 66B are used. Wands 66A, 66B protrude generally horizontally at about the midline of chin table 61, and then curve upwardly to a substantially attitude. Wands 66A, 66B are shaped to be placed on the sides of patient's head, generally between the eyes and the ears, as shown in FIG. 2. To accommodate varying sizes of patient's skulls, wands 66A, 66B are rotatable in the direction shown by arrow A1, each inward in the D1 direction toward the opposite want, and outward in the D2 direction away from the opposite wand, as shown in FIGS. 4-6.

In the embodiment shown in the figures, wands 66A, 66B are rotated using a motor 70. Referring first to FIG. 4, motor 70 is mounted within chin table 61, in the embodiment shown, to bottom cover 62 using a bracket 71 or other similar mechanism for mounting. Motor 70 includes a motor shaft 72, and motor 70 moves shaft 72 in the axial direction as shown by arrow A2. Shaft 72 is coupled to bracket 74, and bracket 74 is coupled to a first pin 76. First pin 76 is coupled to first wand shaft 67A, to which first wand 66A is coupled. Wand shafts 67A, 67B are rotatably mounted to chin table 61, allowing rotation in the directions shown by arrows A3 and A5. When motor 70 moves shaft 73 in direction D1 along arrow A2, bracket 74 moves in direction D1 along A2, which pushes first pin 76 and causes rotation of wand shaft 67A in direction D1 along A3. This is the manner in which motor 70 rotates first wand 66A along arrow A1 between direction D1 and direction D2.

In the most preferred embodiment, bracket 74 includes a paddle 74A which passes through an optical switch 75 mounted to chin table 61 as the bracket 74 is moved by shaft 73. Optical switch 75 acts as a limit switch, stopping motor 70 when the wands 66A, 66B have reached a certain predetermined maximum separation.

Figure 5:
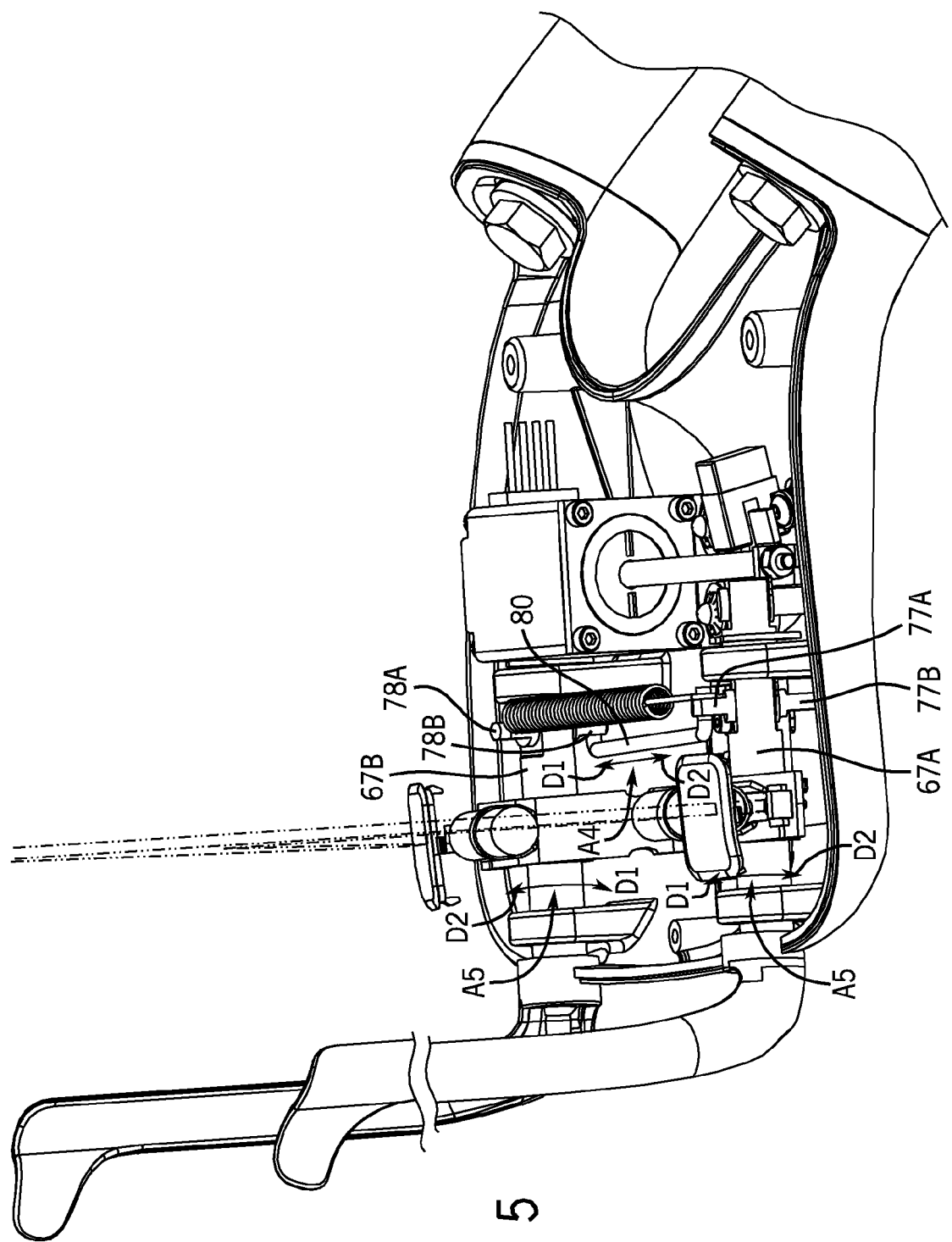
FIG. 5 is a bottom perspective view of a portion the patient positioning arm of a panoramic dental radiation imaging system similar to FIG. 4, but with the wands in a different position.
Figure 6A:
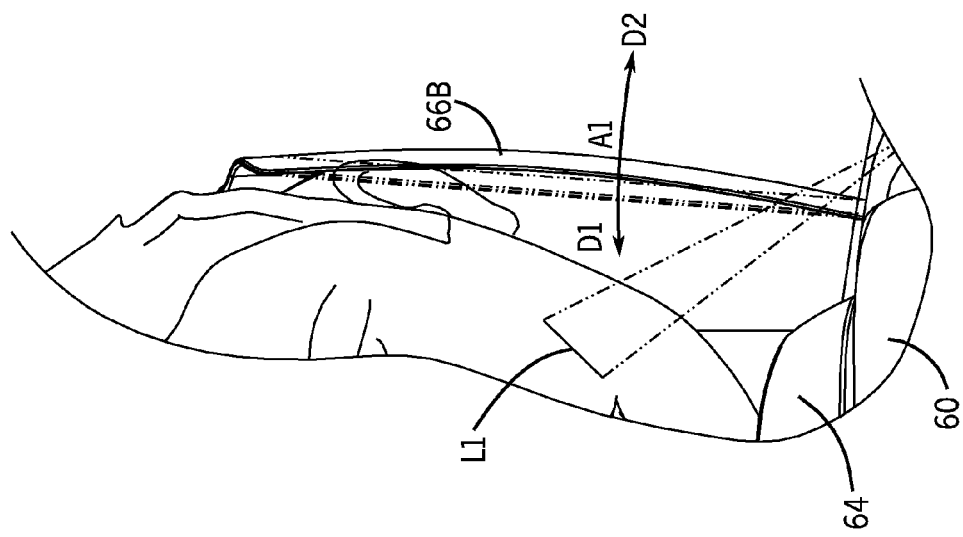
FIG. 6A is a front detail view of one wand of a patient positioning arm, showing alternate positioning of the wand in phantom.
Figure 6:
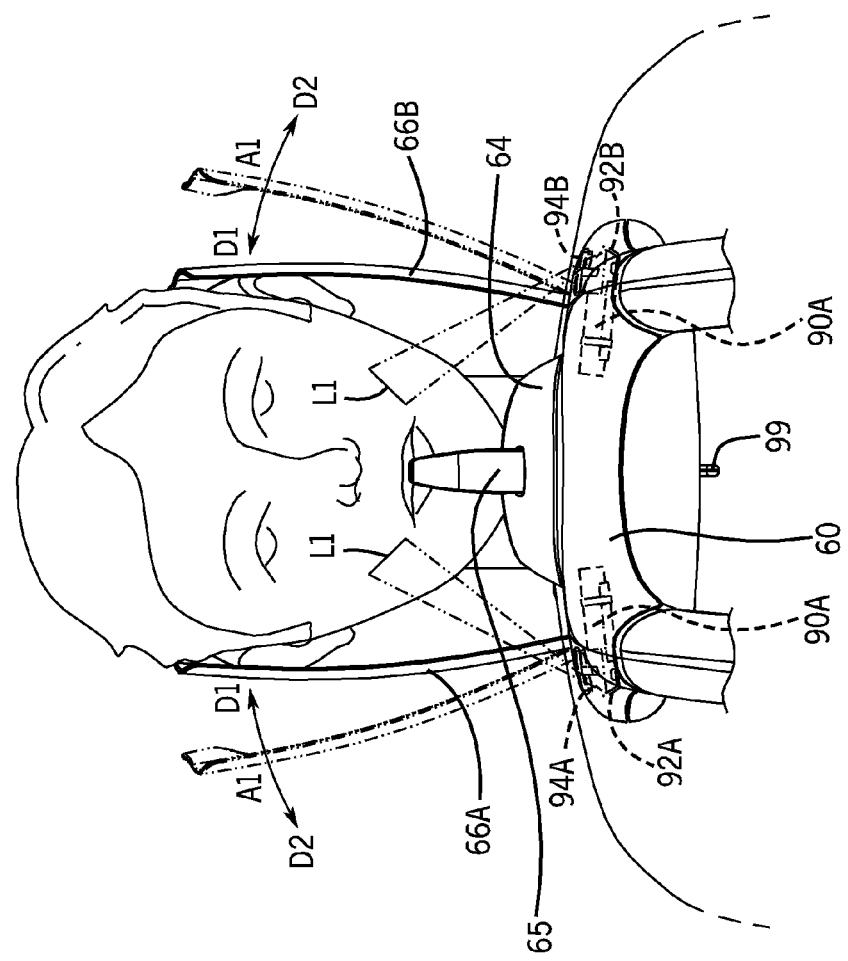
FIG. 6 is a front view of a portion the patient positioning arm of a panoramic dental radiation imaging system in accordance with one embodiment of the present invention, showing a patient being positioned, and showing alternate positioning of the wands in phantom.

Referring now most directly to FIG. 5, a second pin 77 is coupled to first wand shaft 67A, and a third pin 78 is coupled to second wand shaft 67B. Second pin 77 and third pin 78 extend through and beyond wand shafts 67A, 67B, so that a top portion 77A, 78A of each pin 77, 78 extends above each wand shaft 67A, 67B, and a bottom portion 77B, 78B extends below the shafts 67A, 67B. Link bar 80 connects opposite portions of the two pins 77, 78. In the embodiment shown, link bar 80 connects top portion 77A of second pin 77 to bottom potion 78B of third pin 78. Thus when wand shaft 67A rotates in direction D1 along A3, top portion 77A also rotates in direction D1 along arrow A3, which in turn moves link bar 80 in direction D1 along A4. As link bar 80 moves in direction D1 along A3, it pushes bottom portion 78B of pin 78 to rotate wand shaft 67B in direction D1 along A5. The link bar 80 connected to top portion 77A of pin 77 of first wand shaft 67A and bottom portion 78B of second wand shaft 67B thus moves, thereby causing rotation of second wand shaft 67B in the direction opposite to that of first wand shaft 67A. Wands 66A, 66B thus rotate toward each other in direction D1 along arrow A1 when motor 70 moves shaft 72 in direction D1 along A2, and the wands rotate away from each other in direction D2 along arrow A1 when the shaft 72 moves in direction D2 along A2, and the linked movement system ensures that the wands 66A, 66B are moving each at identical angles of rotation and thus that patient's head is not tipped to either the right or left side by any uneven movement of the wands.

Figure 7:
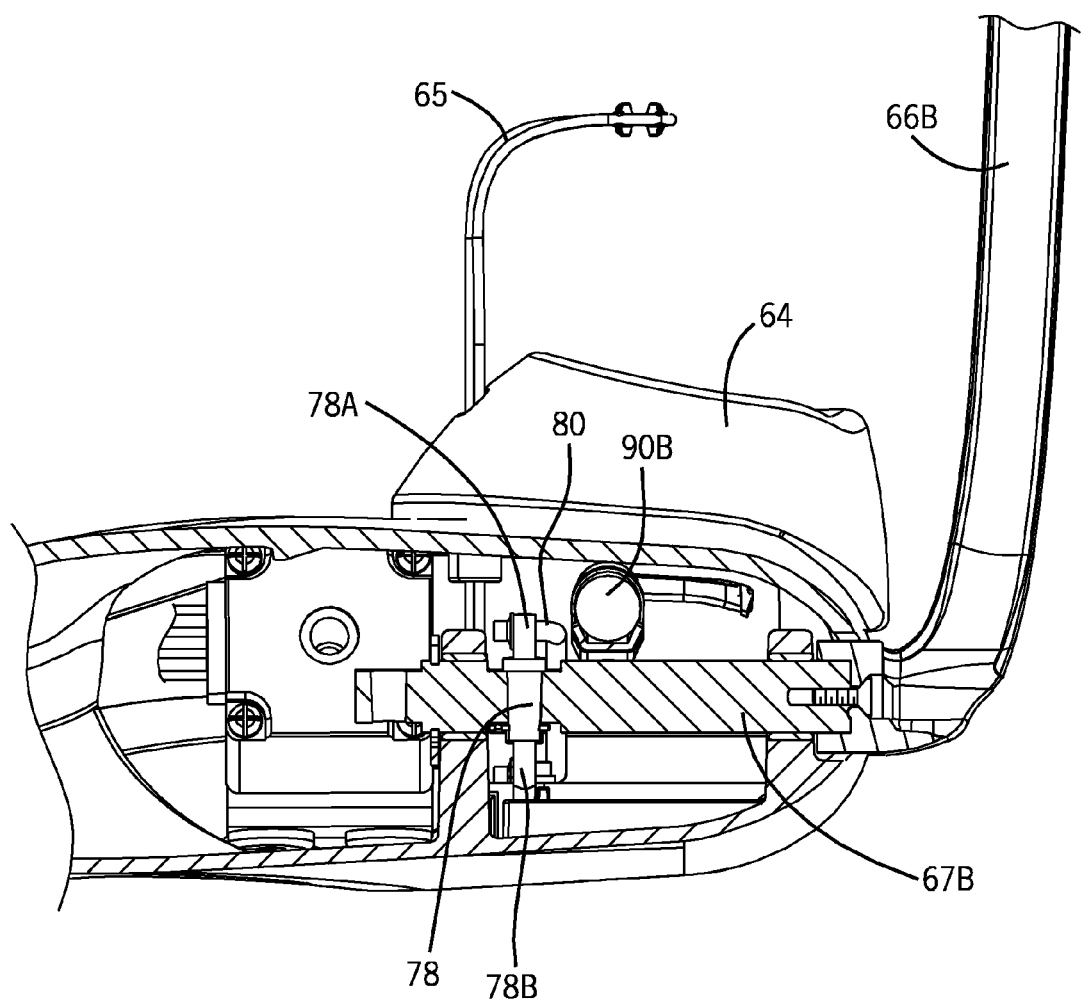
FIG. 7 is a cross sectional view of FIG. 3 taken along line 7-7 thereof.

The connection of link bar 80 to the pins could just as easily be reversed, with the link bar connecting bottom portion 77B of second pin 77 to top portion 78A to third pin 78, as shown in FIG. 7.

Figure 5A:
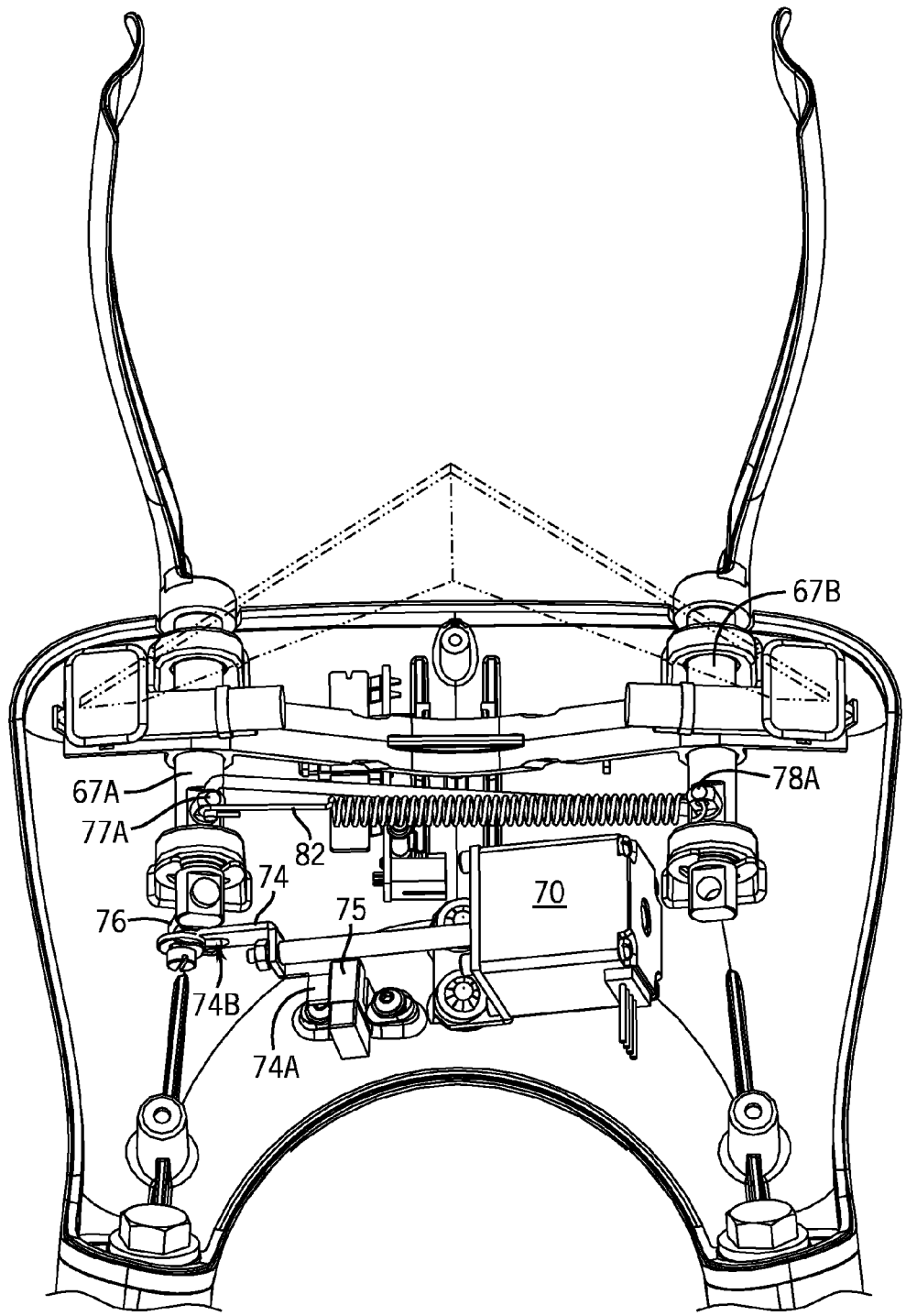

This linked system provides an advantage over current mechanisms, in which guides for positioning of a patient's head are independent of one another and do not provide the even positioning of a linked system. To facilitate use of the wands 66A, 66B, in the embodiment shown, the wands may be manually rotated apart (although not together), against the bias of a spring 82, shown best in FIG. 5A, which is connected between the top portion 77A of pin 77 and top portion 78A of pin 78. Such movement is permitted by a slot 74B by which the bracket 74 is connected to the pin 76. Spring 82 biases the wands 66A, 66B toward each other, the operator can move them apart against the force of spring 82, and the patient may feel the relatively slight force of the biasing on the sides of his or her face.

To further assist in patient positioning, one or more lasers can be used to align the patient's head within the radiation imaging system 10. One set of lasers for proper positioning of the patient may be positioned in the chin table 61, and coupled to the wand system in a certain manner, as shown in FIGS. 3, 4, 6 and 7. In the embodiment shown, cuspid lasers 90A, 90B are coupled to a cuspid slide 98, which is slidably mounted to wand shafts 67A, 67B so as to slide along the shafts axially. Cuspid lasers 90A, 90B are positioned generally horizontally, and generally perpendicular to wand shafts 67A, 67B, with each cuspid laser 90A, 90B aimed at a small mirror 92A, 92B positioned in front of each cuspid laser. The mirrors 92A, 92B are angled so as to direct laser lines upward, through a respective one of lenses 94A, 94B, and project onto the face of the patient near the corners of patient's mouth angled toward the ears, as shown by lines L1 in FIG. 12. The light from each cuspid laser 90A, 90B reflects off each mirror 92A, 92B and through a lens 94A, 94B positioned in the top cover 63 of chin table 61. The entire cuspid slide 98 is movable as a unit along the wand shafts 67A, 67B using cuspid knob 99, which is attached to or preferably integrally formed with cuspid slide 98 and protrudes through bottom cover 62, and moved manually by the technician. As the light from each cuspid laser 90A, 90B is directed through each lens 94A, 94B, the technician moves the cuspid slide 98 to align the laser lines L1 from the cuspid lasers to the appropriate area of the patient's physiognomy. That is, the cuspid slide 98 can adjust the focal trough of the two cuspid lasers 90A, 90B forward or aft to match the patient's dentition.

Figure 7A:
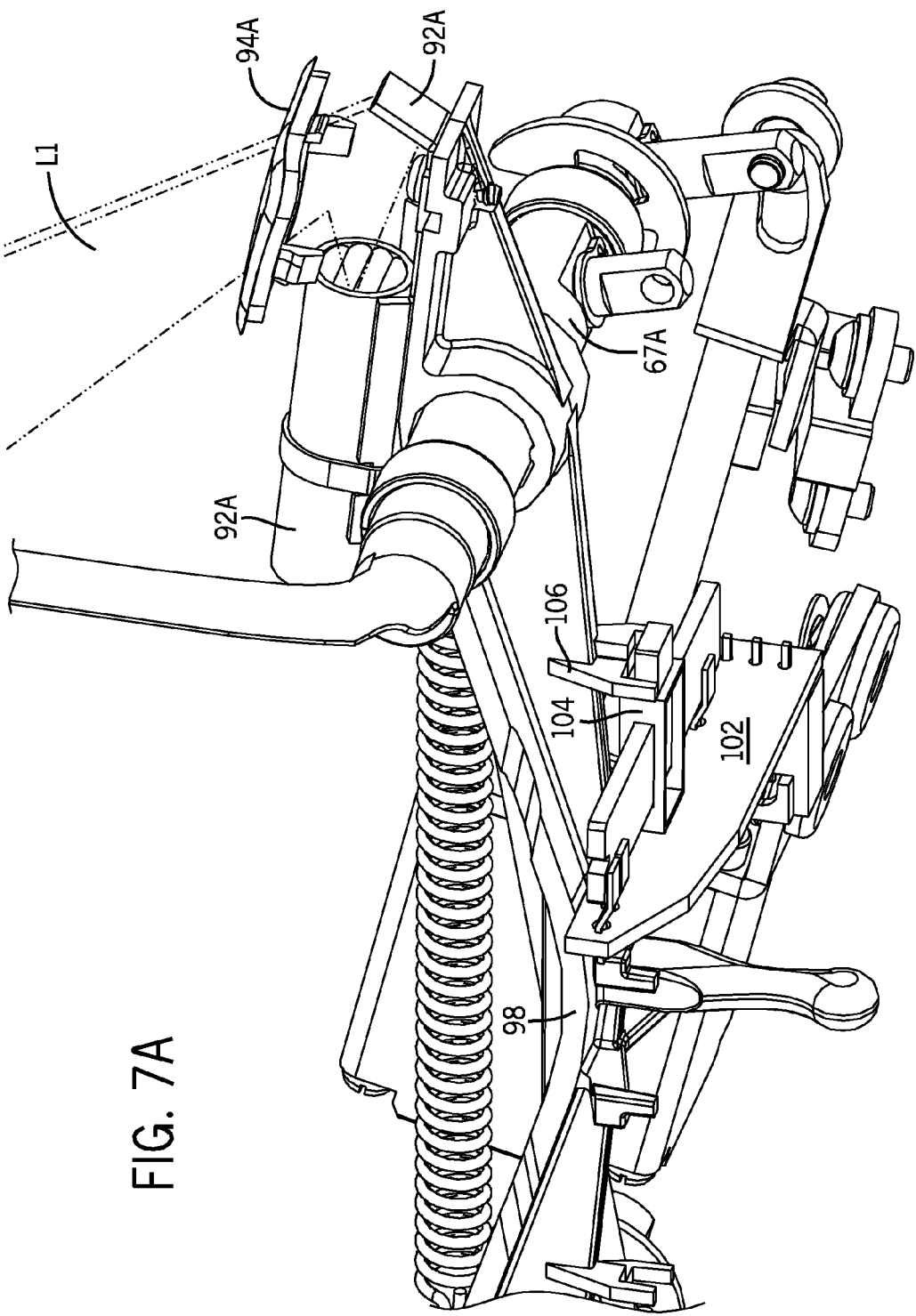

The radiation imaging system 10 receives a signal about the position of the cuspid slide 98, and therefore of the cuspid lasers 90A, 90B by means of a potentiometer 102, shown best in FIG. 7A. Potentiometer 102 is mounted stationary within chin table 61. A potentiometer slider 104 is connected to the cuspid slide 98 by means of a slider mount 106. By this means, movement of the cuspid slide 98 to different positions along the wand shafts 67A, 67B provides a signal, indicating that position. This signal is used, along with the other information gathered by the system, so as to most advantageously position the patient's teeth for imaging.

Additional lasers may be used to ensure proper positioning of the patient, especially the patient's skull, in the radiation imaging system 10. Shown best in FIG. 12, a mid-sagittal laser 100 is located in inner column 30. Mid-sagittal laser 100 is directed to the mid-line of the patient's face, creating a substantially vertical laser line from approximately patient's nose to patient's bottom lip, as shown by the line L1 in FIG. 12. This line L2 helps to position patient in the proper left-right, or X axis, direction, and is most preferably positioned in the center of the philtrum, or infranasal depression, the small vertical groove that exists in the center of the upper lip of most patients.

Figure 12:
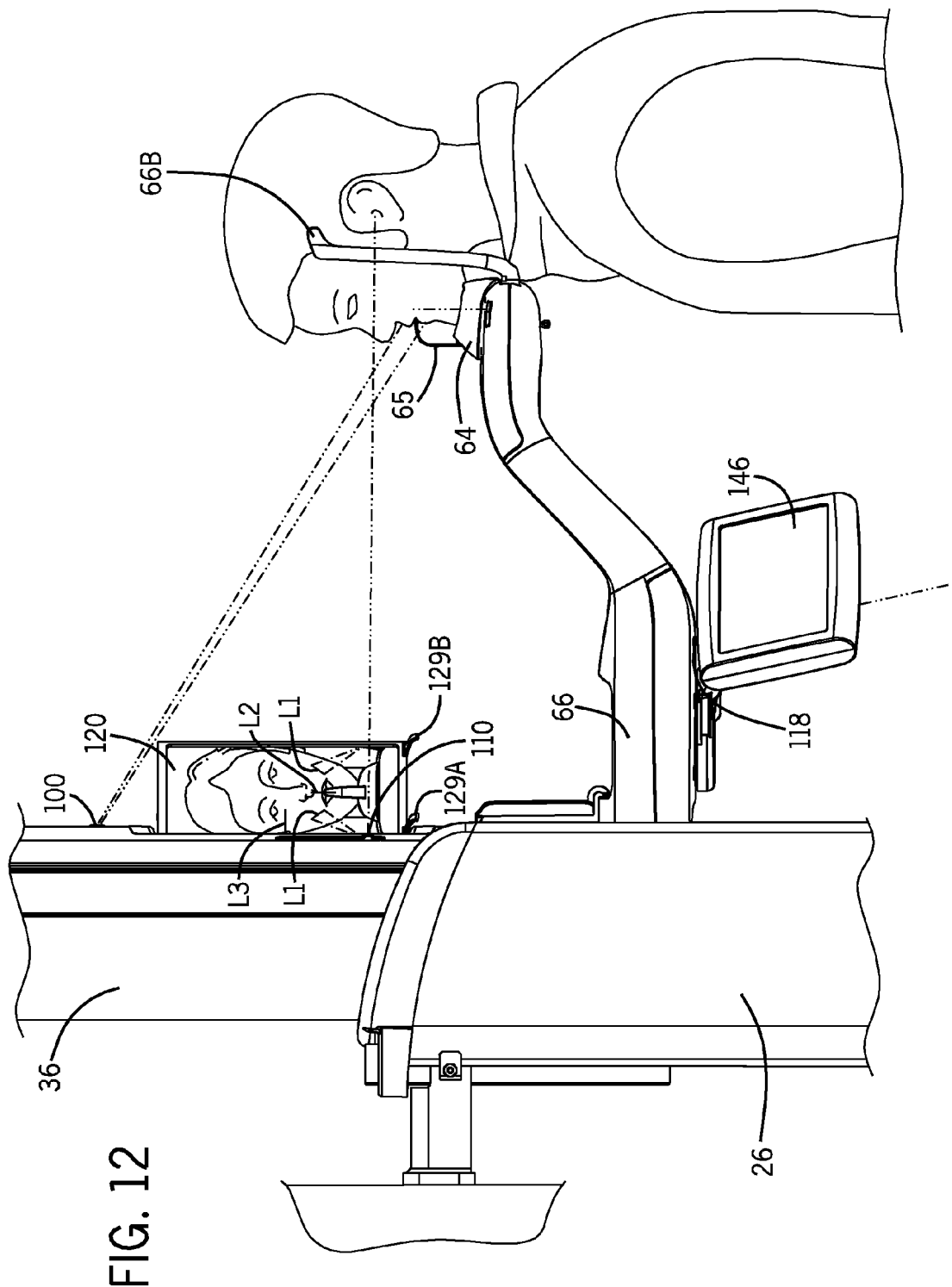
FIG. 12 is a side view of a portion of a panoramic dental radiation system, showing various lasers used for patient positioning.

The most preferred embodiment also includes a Frankfort Plane laser 110, still referring to FIG. 12. The Frankfort Plane laser 110 is movably coupled to inner column 30. A button 112 is slidably coupled to a frame 114, which is mounted behind a slot 116 in inner column 30, and Frankfort Plane laser 110 is mounted to button 112 such that laser light exits through an opening 114 in button 112. As shown in FIG. 12, when button 112 is adjusted to the height of the patient in the direction shown by arrow A6, Frankfort Plane laser 110 creates substantially horizontal line L3 of laser light from approximately the lower edge of the orbit of the eye to the auditory meatus of the ear. This line L3 helps to position patient's head at the proper angle so that the patient's face is not angled too much downward or upward.

A toe laser 118 is located on the underside of patient positioning arm 60. Toe laser 118 projects a laser line L4 to the floor 21 (FIG. 2C), such that patient can align his toes with line L4 projected from toe laser 118 on the floor 21. Line L4 helps to position patient in proper forward-backward, or Y axis, positioning with respect to the radiation imaging system 10. Laser line 118 is probably the first positioning item used by a patient and technician in positioning the patient to use the radiation imaging system 10, as the patient positions his feet properly and comfortably as the first step in positioning his body and head with respect to the imaging system.

Figure 8:
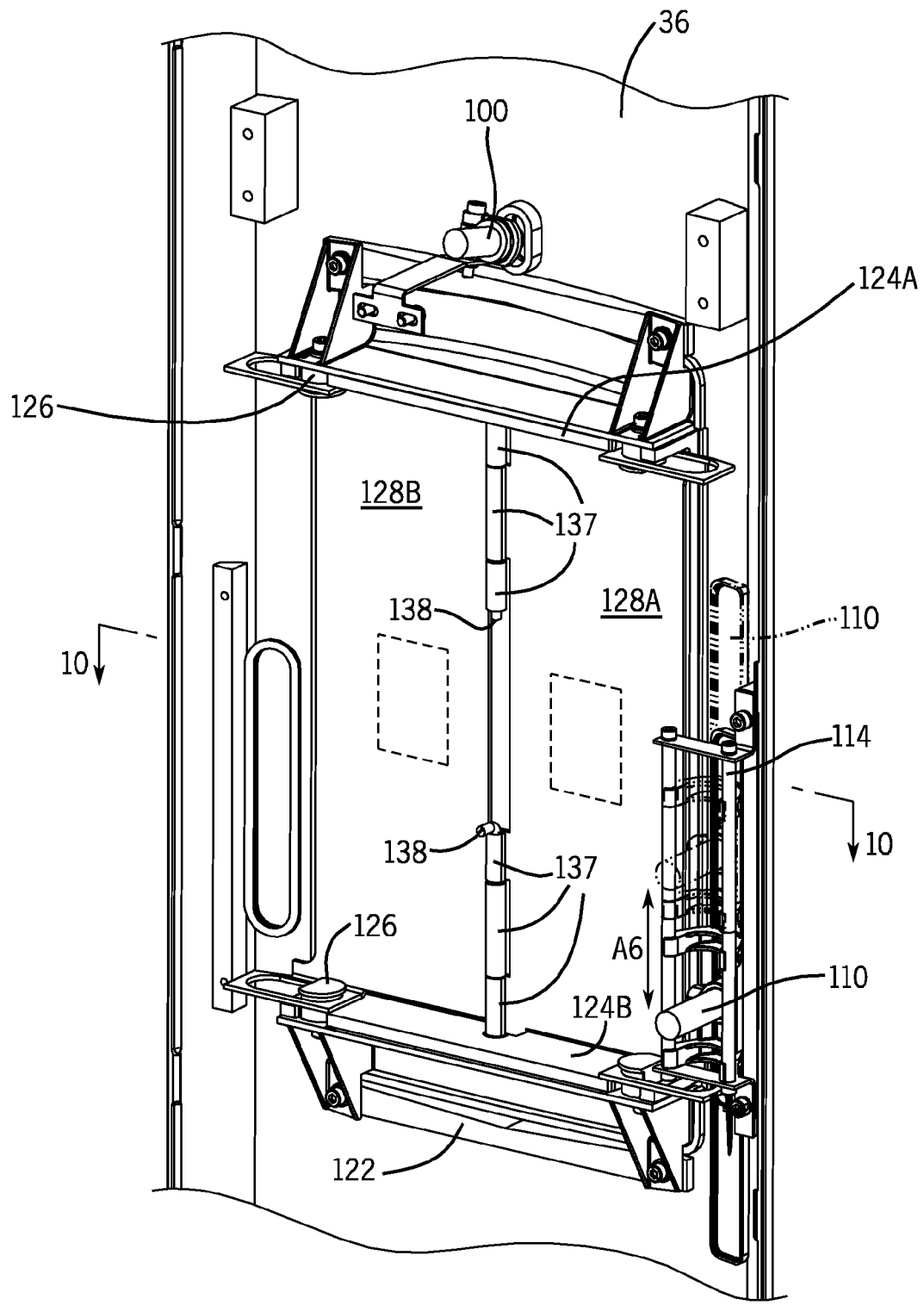
FIG. 8 is a rear perspective view of a portion of the inner column of a panoramic dental radiation imaging system according to an embodiment of the present invention, showing a movable mirror in a flat position.
Figure 9:
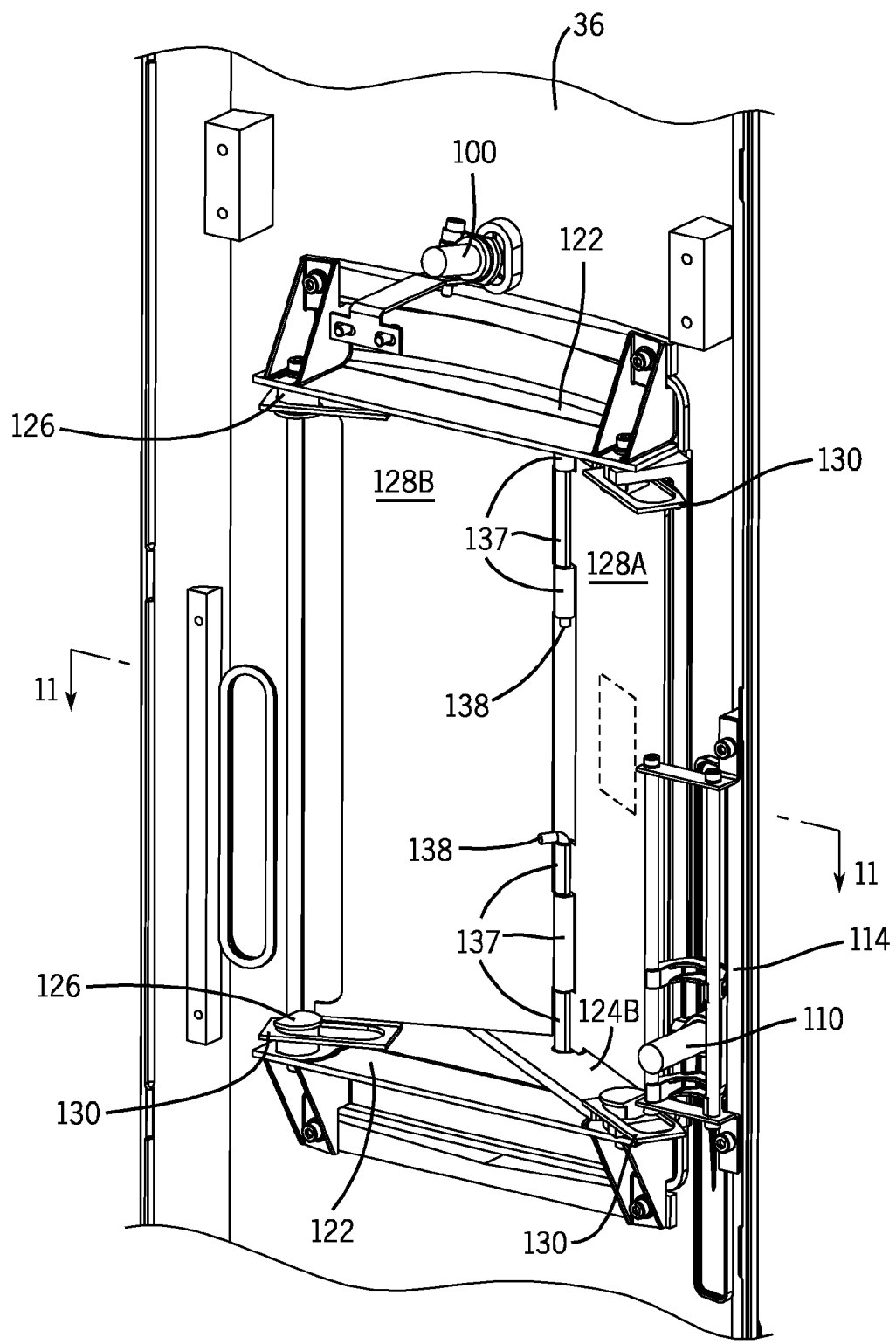
FIG. 9 is a rear perspective view of a portion of the inner column of a panoramic dental radiation imaging system, showing movable mirror in a position angled outward.
Figure 10:
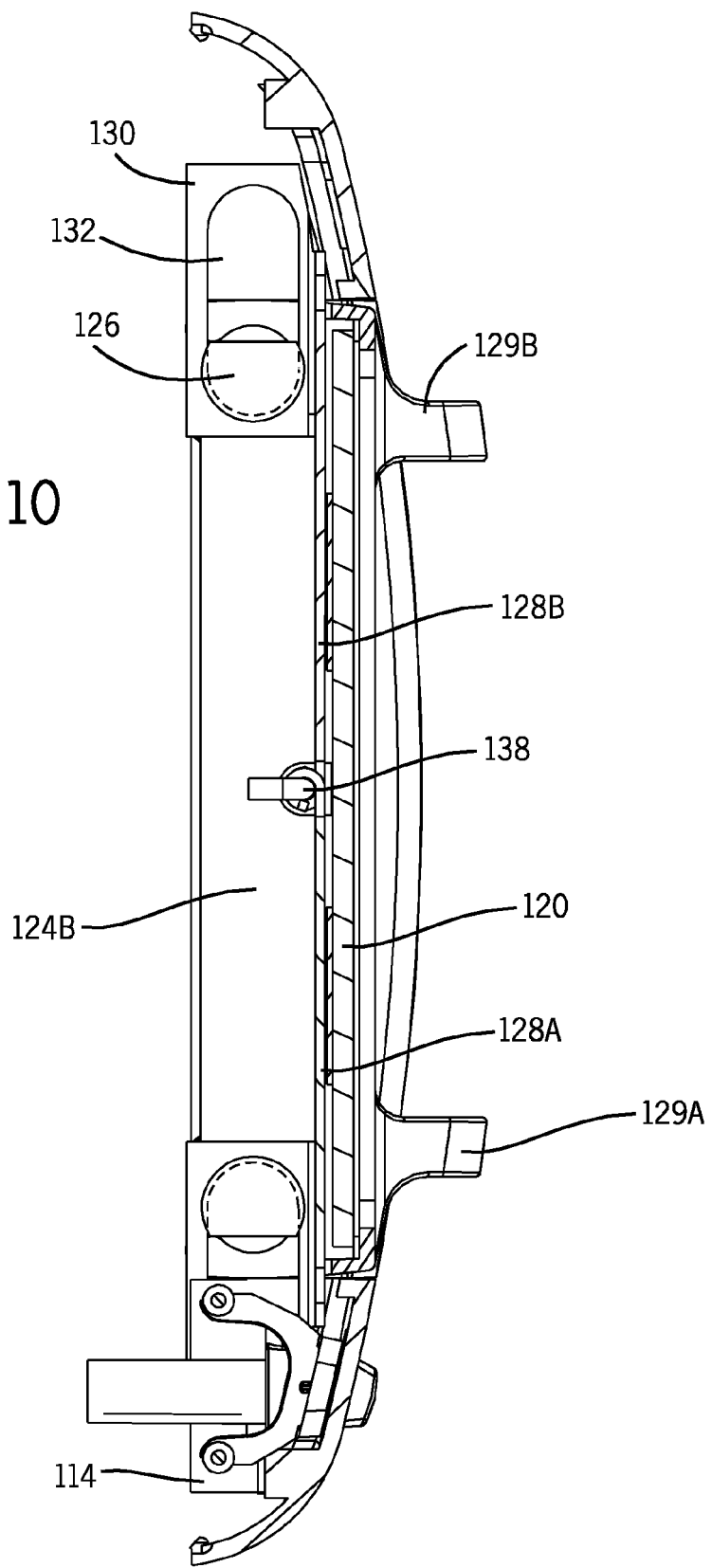
FIG. 10 is a cross section taken along line 10-10 of FIG. 8.
Figure 11:
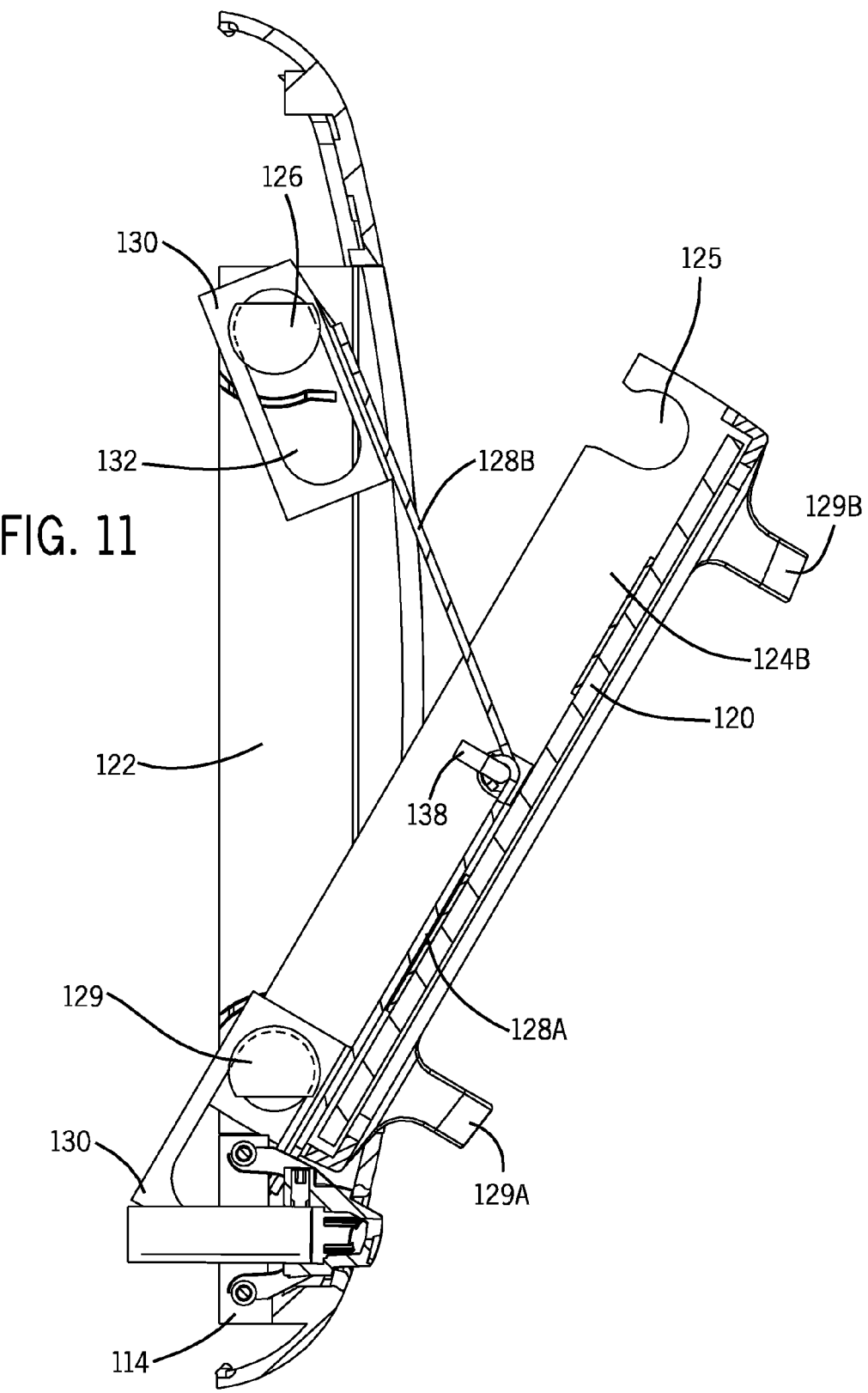
FIG. 11 is a cross section taken along line 11-11 of FIG. 9.

In a preferred embodiment of the invention, a mirror 120 is provided so as to allow a technician to see, in one view of the patient's face, the placement of all of the lasers referred to above that bear on the face. In the embodiment shown, the mirror 120 is mounted to upright support 15, and specifically in this embodiment to inner column 30, using a frame 122 or other suitable means positioned in an opening provided for that purpose in inner column 30. Mirror 120 is positioned such that it generally aligns vertically and horizontally with the patient's face when patient is in place in radiation imaging system 10. It is the mechanism by which mirror 120 is mounted to frame 122 that gives the mirror the capability to be angled, up to 45 degrees or more as shown in FIG. 12, to allow a technician to see the laser placement on patient's face, from either side of the patient positioning arm 60. As shown in FIGS. 8-11, mirror 120 is coupled to a top base member 124A and a bottom base member 124B. Base members 124A, 124B each include a pair of notches 125 which, when minor 120 is in its flat position (FIGS. 8 and 10), each fit around a respective one of a set of posts 126, which are provided for that purpose as part of frame 122. A pair of plates 128A, 128B facilitate movement of mirror 120 to angle the mirror to face more towards one side or the other of positioning arm 60, and are coupled to brackets 130. The brackets 130 have slots 132, which allow brackets 130 to move the distance of the slot length as the brackets 130 slide along posts 126, which in turn allows plates 128A, 128B to move to the angled positions (one of which is shown in FIG. 11). Plates 128A, 128B pivot with respect to each other and base members 124A, 124B by means of a hinge 136, formed by hinge tubes 137 (formed on the plates) and hinge pins 138. Hinge pins 138 pass through openings in base members 124A, 124B besides passing through hinge tubes 137. A pair of tabs 129A, 129B are provided on lower base member 124B, such that when a user pulls on one of the tabs, plates 128A, 128B rotate about hinge pins 138, and the one of the two plates 128A, 128B that is on the same side of hinges 136 as the tab being pulled move corresponding bracket 130, allowing base members 124A, 124B and the mirror 120 coupled thereto to pivot outward to an angle in the direction that the respective tab is pulled. A technician can thus easily see, from the side of the positioning arm 60, that the patient is properly aligned with all laser lines that bear on the patient's face, including the cuspid lasers 90A, 90B, the mid-sagittal laser 100 and the Frankfort Plane laser 110, by simply pulling the one of the tabs 129A, 129B on the side of the lower base member 124B opposite the side he is positioned, so as to angle the mirror 120 in the direction towards him. As shown in FIG. 12, when the technician is positioned to patient's left side, the technician would pull on tab 129B to angle the mirror 120 towards him, and the position of the mirror 120 and associated components in the angled position would become that shown in FIG. 11. Once alignment is achieved, the one tab of tabs 129A, 129B which had been pulled is pushed back toward inner column 30 to return mirror 120 to its flat position, as shown in FIG. 10. At that point, in its flat position as shown in FIGS. 8 and 10, the mirror 120 allows a patient to see himself and helps the patient maintain the proper alignment achieved with wands 66A, 66B, cuspid lasers 90A, 90B, mid-sagittal laser 100 and Frankfort Plane laser 110, once set by the technician.

A movable display screen 140 may also be coupled to patient positioning arm 50. The screen 140 may be rotatable, such that a user or technician could rotate the screen below the patient positioning arm 60 to either side of the patient positioning arm. This would allow the technician to read the positioning, radiation activity, or other desired information from either side of radiation imaging system 10.

The most preferred form of the radiation referred to in this description is x-radiation, but there may be other types of radiation, whether now known or later discovered, that would work as well.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A patient positioning system for a panoramic dental radiation imaging system, the imaging system having a radiation source and a radiation sensor, the positioning system comprising:
   an upright support supporting the radiation source and radiation sensor;
   a patient positioning arm mounted to the upright support;
   a pair of motorized wands rotatably connected to the patient positioning arm and connected together so as to move at identical angles of inclination with respect to each other but in opposite directions;
   a pair of cuspid lasers, each projecting a laser line directed at a respective side of a patient's face near the patient's mouth and angled generally toward the patient's ears to identify where a technician is to position a patient's dentition in the proper position for the functioning of the imaging system;
   a movable member supporting the cuspid lasers; and
   a sensing device sensing the position of the movable member to thereby sense the position of the cuspid lasers.

2. A patient positioning system as recited in claim 1 further comprising a chin rest mounted to the patient positioning arm, on which the patient may rest his or her chin.

3. A patient positioning system as recited in claim 1 further comprising a toe laser, projecting a line of light on a floor in front of the patient to assist the patient to position his toes, and thereby his body, as desired with respect to the imaging system.

4. A patient positioning system as recited in claim 1 further comprising a mid-sagittal laser, projecting a line of light onto the mid-sagittal area of patient's face to assist the technician to position the patient's head as desired with respect to the imaging system.

5. A patient positioning system as recited in claim 1 further comprising a Frankfort Plane laser, projecting a line of light onto the Frankfort Plane area of the patient's face to assist the technician to position the patient's head as desired with respect to the imaging system.

6. A patient positioning system as recited in claim 1 further comprising a mirror positioned on the upright support so as to enable the technician to see one or more lasers on the patient's face to assist the technician to position the patient's head as desired with respect to the imaging system.

7. A patient positioning system as recited in claim 6 wherein the mirror is mounted to the upright support by a mechanism that permits the mirror to be rotated outward from the upright support, in two directions, up to 45 degrees, so as to enable the technician to see one or more lasers on the patient's face from the technician's position on either side of the positioning arm.

8. A patient positioning system as recited in claim 1, further comprising a biasing member biasing the motorized wands in a direction toward one another.

9. A panoramic dental radiation imaging system comprising:
- a radiation source;
- a radiation sensor, an upright support supporting the radiation source and radiation sensor; and
- a patient positioning system, comprising:
- a patient positioning arm mounted to the upright support;
- a pair of motorized wands rotatably connected to the patient positioning arm and connected together so as to move at identical angles of inclination with respect to with each other but in opposite directions;
- a pair of cuspid lasers, each providing a laser line directed at a respective side of a patient's face near the patient's mouth and angled generally toward the patient's ears, thereby permitting a technician to position for the functioning of the imaging system;
- a movable member supporting the cuspid lasers; and
- a sensing device sensing the position of the movable member to thereby sense the position of the cuspid lasers.

10. A patient positioning system as recited in claim 9 further comprising a chin rest mounted to the patient positioning arm, on which the patient may rest his or her chin.

11. A patient positioning system as recited in claim 9 further comprising a toe laser, projecting a line of light on a floor in front of the patient to assist the patient to position his toes, and thereby his body, as desired with respect to the imaging system.

12. A patient positioning system as recited in claim 9 further comprising a mid-sagittal laser, projecting a line of light onto the mid-sagittal area of patient's face to assist the technician to position the patient's head as desired with respect to the imaging system.

13. A patient positioning system as recited in claim 9 further comprising a Franklin plain laser, projecting a line of light onto the Franklin plain area of the patient's face to assist the technician to position the patient's head as desired with respect to the imaging system.

14. A patient positioning system as recited in claim 9 further comprising a mirror positioned on the upright support so as to enable the technician to see one or more lasers on the patient's face to assist the technician to position the patient's head as desired with respect to the imaging system.

15. A patient positioning system as recited in claim 9, further comprising a biasing member biasing the motorized wands in a direction toward one another.

* * * * *

UNITED STATES PATENT AND TRADEMARK OFFICE
CERTIFICATE OF CORRECTION

PATENT NO. : 8,509,381 B2
APPLICATION NO. : 12/638600
DATED : August 13, 2013
INVENTOR(S) : Donald Walker et al.

It is certified that error appears in the above-identified patent and that said Letters Patent is hereby corrected as shown below:

In the Specification:

Column 3,
Lines 1-2 read "view of a portion the patient" and should read -- view of a portion of the patient --.

Column 3,
Line 7 reads "view of a portion the patient" and should read -- view of a portion of the patient --.

Column 3,
Line 11 reads "view of a portion the patient" and should read -- view of a portion of the patient --.

Column 3,
Line 15 reads "view of a portion the patient" and should read -- view of a portion of the patient --.

Column 3,
Line 31 reads "showing movable mirror in a" and should read -- showing a movable mirror in a --.

Column 4,
Lines 53-54 reads "and then curve upwardly to a substantially attitude" and should read -- and then curve upwardly to a substantially vertical attitude --.

Column 4,
Line 58 reads "the opposite want, and" and should read -- the opposite wand, and --.

In the Claims:

Claim 9, Column 9
Lines 16-17 read "move at identical angles of inclination with respect to with each other but in" and should read -- move at identical angles of inclination with respect to each other but in --.

Signed and Sealed this
Nineteenth Day of November, 2013

Teresa Stanek Rea
*Deputy Director of the United States Patent and Trademark Office*

CERTIFICATE OF CORRECTION (continued)
U.S. Pat. No. 8,509,381 B2

Claim 9, Column 9
Line 21 reads "thereby permitting a technician to position for the" and should read -- thereby permitting a technician to position a patient's dentition for the --.

Claim 13, Column 10
Line 15 reads "further comprising a Franklin plain laser" and should read -- further comprising a Frankfort plane laser --.

Claim 13, Column 10
Line 16 reads "light onto the Franklin plain area" and should read -- light onto the Frankfort plane area --.